US007150992B1

(12) United States Patent
Lynch et al.

(10) Patent No.: US 7,150,992 B1
(45) Date of Patent: Dec. 19, 2006

(54) METHODS OF PREPARING DENDRITIC CELLS WITH FLT3-LIGAND AND ANTIGEN

(75) Inventors: David H. Lynch, Bainbridge Island, WA (US); Kenneth A. Brasel, Seattle, WA (US); Hilary J. McKenna, Seattle, WA (US); Luis G. Borges, Seattle, WA (US); Charles R. Maliszewski, Seattle, WA (US); Eugene Maraskovsky, Victoria (AU)

(73) Assignee: Innunex Corporation, Seattle, WA (US)

( * ) Notice: Subject to any disclaimer, the term of this patent is extended or adjusted under 35 U.S.C. 154(b) by 0 days.

(21) Appl. No.: 09/699,923

(22) Filed: Oct. 30, 2000

Related U.S. Application Data

(60) Division of application No. 09/154,903, filed on Sep. 17, 1998, now abandoned, which is a continuation-in-part of application No. 08/725,540, filed on Oct. 3, 1996, now abandoned, which is a continuation-in-part of application No. 08/539,142, filed on Oct. 4, 1995, now abandoned.

(51) Int. Cl.
*C12N 5/02* (2006.01)
*C12N 5/06* (2006.01)
*C12N 5/08* (2006.01)

(52) U.S. Cl. .......................... 435/377; 435/2; 435/325; 435/375

(58) Field of Classification Search .................. 435/2, 435/7.1, 375
See application file for complete search history.

(56) References Cited

U.S. PATENT DOCUMENTS

| 4,745,099 A | 5/1988 | Akamatsu et al. |
| 5,013,824 A | 5/1991 | Abrams et al. |
| 5,057,420 A | 10/1991 | Massey |
| 5,061,620 A | 10/1991 | Tsukamoto et al. |
| 5,114,710 A | 5/1992 | Takaku et al. |
| 5,116,964 A | 5/1992 | Capon et al. |
| 5,185,438 A | 2/1993 | Lemischka |
| 5,192,553 A | 3/1993 | Boyse et al. |
| 5,199,942 A | 4/1993 | Gillis |
| 5,270,458 A | 12/1993 | Lemischka |
| 5,283,354 A | 2/1994 | Lemischka |
| 5,326,558 A | 7/1994 | Turner et al. |
| 5,367,057 A | 11/1994 | Lemischka |
| 5,397,706 A | 3/1995 | Correa et al. |
| 5,399,493 A | 3/1995 | Emerson et al. |
| 5,437,994 A | 8/1995 | Emerson et al. |
| 5,453,357 A | 9/1995 | Hogan |
| 5,459,069 A | 10/1995 | Palsson et al. |
| 5,525,708 A | 6/1996 | Nocka et al. |
| 5,548,065 A | 8/1996 | Lemischka |
| 5,554,512 A | 9/1996 | Lyman et al. |
| 5,627,025 A | 5/1997 | Steinman et al. |
| 5,635,388 A | 6/1997 | Bennett et al. |
| 5,843,423 A | 12/1998 | Lyman et al. |
| 5,914,108 A * | 6/1999 | Tsukamoto et al. ........ 424/93.7 |
| 5,994,126 A * | 11/1999 | Steinman et al. |
| 6,015,554 A * | 1/2000 | Galy et al. |

FOREIGN PATENT DOCUMENTS

| CA | 2163105 | 5/1994 |
| EP | 0 563 485 A1 | 3/1992 |
| EP | 0 627 487 A2 | 5/1994 |
| WO | WO 92/18615 | 10/1992 |
| WO | WO 93/08268 | 4/1993 |
| WO | WO 93/20186 | 10/1993 |
| WO | WO 94/26891 | 11/1994 |
| WO | WO 94/28391 | 12/1994 |
| WO | WO 95/00554 | 1/1995 |
| WO | WO 96/00779 | 1/1996 |

OTHER PUBLICATIONS

Stanley, E. R. et al., "CSF-1-A Mononuclear Phagocyte Lineage-Specific Hemopoietic Growth Factor," *J. Cell. Bio.* 21:151-159, 1983.
Y. Yarden and A. Ullrich, "Growth Factor Receptor Tyrosine Kinases," *Ann. Rev. Biochem.* 57:443-478, 1988.
J. G. Flanagan and P. Leder, "The kit Ligand: A Cell Surface Molecule Altered in Steel Mutant Fibroblasts," *Cell* 63:185-194, 1990.
D. Cadena and G. Gill, "Receptor tyrosine kinases," *FASEB* 6:2332-2337, 1992.
Matthews, W. et al., "A Receptor Tyrosine Kinase Specific to Hematopoietic Stem and Progenitor Cell-Enriched Populations," *Cell* 65:1143-1152, 1991.
Lyman, S. D. et al., "Characterization of the protein encoded by the flt3 (flk2) receptor-like tyrosine kinase gene," *Oncogene* 8:815-822, 1993.
Rosnet, O. et al., "Isolation and Chromosomal Localization of a Novel FMS-like Tyrosine Kinase Gene," *Genomics* 9:380-385, 1991.

(Continued)

*Primary Examiner*—Phillip Gambel
(74) *Attorney, Agent, or Firm*—Sughrue Mion, PLLC

(57) ABSTRACT

Flt3-ligand can be used to generate large numbers of dendritic cells from hematopoietic progenitor and stem cells. Flt3-ligand can be used to augment immune responses in vivo, and expand dendritic cells ex vivo. Such dendritic cells can then be used to present tumor, viral or other antigens to naive T cells, can be useful as vaccine adjuvants. When flt3-L is used and/or administered in combination with other reactive agents, e.g. CD40 binding proteins and 4-1BBL or antibodies reactive with 4-1BB, the combination further enhances immune responses and the effectiveness of vaccine adjuvants.

5 Claims, No Drawings

OTHER PUBLICATIONS

Lyman, Stewart D. et al., "Molecular Cloning of a Ligand for the flt3/flk-2 Tyrosine Kinase Receptor: A Proliferative Factor for Primitive Hematopoietic Cells," *Cell* 75:1157-1167, 1993.

Maroc, N. et al., "Biochemical characterization and analysis of the transforming potential of the FLT3/FLK2 receptor tyrosine kinase," *Oncogene* 8:909-918, 1993.

Birg, F. et al., "Expression of the *FMS/KIT*-Like Gene *FLT3* in Human Acute Leukemias of the Myeloid and Lymphoid Lineages," *Blood* 80 (10):2584-2593, 1992.

Dosil, M. et al, "Mitogenic Signalling and Substrate Specificity of the Flk2/Flt3 Receptor Tyrosine Kinase in Fibroblasts and Interleukin 3-Dependent Hematopoietic Cells," *Mol. And Cell. Biol.* 13(10):6572-6585 1993.

Hannum, C. et al., "Ligand for FLT3/FLK2 receptor tyrosine kinase regulates growth of haematopoietic stem cells and is encoded by variant RNAs," *Nature* 368:643-648, 1994.

Broxmeyer, H. E. et al., "*Commentary*: A Rapid Proliferation Assay for Unknown Co-Stimulating Factors in Cord Blood Plasma Possibly Involved in Enhancement of In Vitro Expansion and Replating Capacity of Human Hematopoietic Stem/Progenitor Cells," *Blood Cells* 20:492-497, 1994.

de Vries, P. et al., "The Effect of the FLT3 Ligand On Purified Murine Pluripotent Hematopoietic Stem Cells," *J. of Cell. Biochem. Suppl.* 18b:177, abstract #H110, 1994.

Rossner, M. T. et al., "Fms-like Tyrosine Kinase 3 Catalytic Domain Can Transduce a Proliferative Signal in FDC-P1 Cells That is Qualitatively Similar to the Signal Delivered by c-Fms$^1$," *Cell Growth & Differentiation* 5 :549-555, 1994.

Small. D. et al., "STK-1, the human homolog of Flk-2/Flt-3, is selectively expressed in CD34$^+$ human bone marrow cells and is involved in the proliferation of early progenitor of early progenitor/ stem cells," *Proc. Natl. Acad. Sci. USA* 91:459-463, 1994.

Zeigler, F. C. et al., "Cellular and Molecular Characterization of the Role of the FLK-2/FLT-3 Receptor Tyrosine Kinase in Hematopoietic Stem Cells," *Blood* 84(8):2422-2430, 1994.

de Vries, P. et al., "The Role of FLT3 Ligand in Early Murine Hematopoiesis," *Blood* 84 (10) Suppl. I:279a, abstract #1100, 1994.

de Vries, P. et al., "The Effects of Soluble FLT3 Ligand On Murine Pluripotent Hematopoietic Stem Cells," *Experimental Hematology* 22(8):724, abstract #174, 1994.

Stewart, F. M. et al., "Post-5-Fluorouracil Human Marrow: Stem Cell Characteristics and Renewal Properties After Autologous Marrow Transplantation," *Blood* 81(9):2283-2289, 1993.

Bernhard, H. et al., "Generation of Immunostimulatory Dendritic Cells from Human CD34+Hematopoietic Progenitor Cells of the Bone Marrow and Peripheral Blood," *Cancer Res.* 55:1099-1104, 1995.

Chatterjee, M. et al., "Idiotypic antibody immunotherapy of cancer," *Cancer Immunol. Immunotherap.* 38:75-82. 1994.

Boon, T., "Toward a Genetic Analysis of Tumor Rejection Antigens," *Adv. Cancer Res.* 58:177-211, 1992.

McBride, G., "New Molecule Under Study: Flt3 Ligand May Mobilize Dendritic Cells," *J. Nat'l Cancer Inst.* 89(17):1257, 1997.

Pulendran, B. et al., "Developmental Pathways of Dendritic Cells in Vivo: Distinct Function, Phenotype, and Localization of Dendritic Cell Subsets in FLT3 Ligand-Treated Mice," *J. Immunol.* 159(5):2222-2231, 1997.

Shurin, M. et al., "FLT3 Ligand Induces the Generation of Functionally Active Dendritic Cells in Mice," *Cell. Immunol.* 179(2):174-184, 1997.

Chen, K. et al., "Antitumor Activity and Immunotherapeutic Properties of Flt3-Ligand in a Murine Breast Cancer Model," *Cancer Res.* 57(16):3511-3516, 1997.

Strobl, H. et al., "flt3 Ligand in Cooperation with Transforming Growth Factor-β1 Potentiates In Vitro Development of Langerhans-Type Dendritic Cells and Allows Single-Cell Dendritic Cell Cluster Formation Under Serum-Free Conditions," *Blood*, 90(4):1425-1434, 1997.

Juan, T. et al., "Chronic Expression of Murine flt3 Ligand in Mice Results in Increased Circulating White Blood Cell Levels and Abnormal Cellular Infiltrates Associated With Splenic Fibrosis," *Blood* 90(1):76-84, 1997.

Lynch, D. et al., "Flt3 ligand induces tumor regression and antitumor immune responses *in vivo*," *Nature Med.* 3(6):625-631, 1997.

Saunders, D. et al., "Dendritic Cell Development in Culture from ThymicPprecursor Cells in the Absence of Granulocyte/Macrophage Colony-stimulating Factor," *J. Exp. Med.* 184:2185-2196, 1996.

Maraskovsky, E. et al., "Dramatic Increase in the Numbers of Functionally Mature Dendritic Cells in Flt3 Ligand-treated Mice: Multiple Dendritic Cell Subpopulations Identified," *J. Exp. Med.* 184:1953-1962, 1996.

E. Sprecher and Y. Becker, "Role of Langerhans cells and other dendritic cells in viral diseases," *Arch. Virol.* 132:1-28, 1993.

Broxmeyer, H. et al., "Flt3 ligand stimulates/costimulates the growth of myeloid stem/progenitor cells," *Exp. Hematol.* 23:1121-1129, 1995.

A. Porgador and E. Gilboa, "Bone marrow-generated Dendritic Cells Pulsed with a Class I-restricted Peptide are Potent Inducers of Cytotoxic T Lymphocytes," *J. Exp. Med.* 182:255-260, 1995.

Hudak, S. et al., "FLT3/FLK2 Ligand Promotes The Growth Of Murine Stem Cells And The Expansion of Colony-Forming Cells And Spleen Colony-Forming Units," *Blood* 85(10):2747-2755, 1995.

Muench, M. et al., "FLK-2/FLT-3 Ligand Regulates The Growth Of Early Myeloid Progenitors Isolated From Human Fetal Liver," *Blood* 85(4):963-972, 1995.

Steinman, R., "The Dendritic Cell System and Its Role in Immunogenicity," *Annu. Rev. Immunol.* 9:271-296, 1991.

Macatonia, S. et al., "Primary proliferative and cytotoxic T-cell responses to HIV induced *in vitro* by human dendritic cells," *Immunology* 74:399-406, 1991.

Pancholi, P. et al., "Dendritic Cells Efficiently Immunoselect Mycobacterial-Reactive T Cells In Human Blood, Including Clonable Antigen-Reactive Precursors," *Immunology* 76:217-224, 1992.

Inaba, K. et al., "Dendritic Cells Pulsed With Protein Antigens In Vitro Can Prime Antigen-Specific, MHC-Restricted T Cells In Situ," *J. Exp. Med.* 172:631-640, 1990.

Bujdoso, R. et al., "Afferent Lymph Dendritic Cells: A Model For Antigen Capture And Presentation In *Vivo*," *Intern. Rev. Immunol.* 6:177-186, 1990.

Jaffe, R., "Review Of Human Dendritic Cells: Isolation And Culture From Precursors," *Pedriatic Pathology* 13:821-837, 1993.

Bermstein, I. et al., "Isolation Of Human Hematopoietic Stem Cells," *Blood Cells* 20:15-24, 1994.

Young, J. et al., "identification Of Dendritic Cell Colony-Forming Units Among Normal Human CD34$^+$ Bone Marrow Progenitors That Are Expanded By C-Kit Ligand And Yield Pure Dendritic Cell Colonies In The Presence Of Granulocyte/Macrophage Colony-Stimulating Factor And Tumor Necrosis Factor α," *J. Exp. Med.* 182:1111-1120, 1995.

Inaba, K. et al., "Dendritic Cell Progenitors Phagocytose Particulates, Including Bacillus Calmette-Guerin Organisms, And Sensitize Mice To Mycobacterial Antigens In Vivo," *J. Exp. Med.* 178479-488, 1993.

Papayannopoulo et al., "In Vivo Effects of Flt3/Flk2 Ligand on Mobilization of Hematopoietic Progenitors in Primates and Potent Synergistic Enhancement With Granulocyte Colony-Stimulating Factor," *Blood* 90:620-629, 1997.

Lotem, J. and Sachs, L., "Control of In Vivo Differentiation of Myeloid Leukemic Cells," *Leukemia* 2(12 Suppl.):24S-37S, 1988.

Stewart D. Lyman et al., "Cloning of the Human Homologue of the Murine flt3 Ligand: A Growth Factor for Early Hematopoietic Progenitor Cells," *Blood* 83(10):2795-2801, 1994.

D. Hanahan, "Transgenic Mice as Probes into Complex Systems," *Science* 246:1265-1275, 1989.

Romani, N. et al., "Proliferating Dendritic Cell Progenitors in Human Blood," *J. Exp. Med.* 180:83-93, 1994.

Winton, E. F. et al., "Recombinant Human (rh) FLT3 Ligand Plus rhGM-CSF or rhG-CSF Causes a Marked CD34$^+$ Cell Mobilization to Blood in Rhesus Monkeys," ASH Abstract, Dec. 1996.

F. Sallusto and A. Lanzavecchia, "Efficient Presentation of Soluble Antigen by Cultured Human Dendritic Cells is Maintained by Granulocyte/Macrophage Colony-stimulating Factor Plus Interleukin 4 and Downregulated by Tumor Necrosis Factor α," *J. Exp. Med.* 179:1109-1118, 1994.

Szabolcs, P. et al, "Expansion of Immunostimulatory Dendritic Cells Among the Myeloid Progeny of Human CD34$^+$ Bone Marrow Precursors Cultured with c-kit Ligand, Granulocyte-Macrophage Colony-Stimulating Factor, and TNF-α," *J. Immunl.* 154:5851-5861, 1995.

Rosnet, O. et al., "Murine Flt3, a gene encoding a novel tyrosine kinase receptor of the PDGFR/CSF1R family," *Oncogene* 6:1641-1650, 1991.

S. Stengelin et al., "Isolation of cDNAs for two distinct human Fc receptors by ligand affinity cloning," *EMBO J.* 7(4):1053-1059, 1988.

Debets, R. and Savelkoul, H. F. J. "Cytokine antagonists and their potential therapeutic use," *Immunol. Today* 15(10):455-458, 1994.

Small et al., "STK-1 is Expressed in a Subpopulation of Human Bone Marrow Enriched for CD34$^+$ Progenitor/Stem Cells and in a Number of Leukemic Cell Lines," *Blood* 80, 296a; Abstract No. 1175, 1992.

Reid, D. L. et al., "Interactions Of Tumor Necrosis Factor With Granulocyte-Macrophage Colony-Stimulating Factor And Other Cytokines In The Regulation Of Dendritic Cell Growth In Vitro From Early Bipotent CD34$^+$ Progenitors In Human Bone Marrow," *J. of Immunol.* 149(8):2681-2688,1992.

Thomson, A. W. et al., "Microchimerism, Dendritic Cell Progenitors and Transplantation Tolerance," *Stem Cells* 13:622-639, 1995.

Lyman, S. D. and Jacobsen, S. E. W., "c-kit Ligand and Flt-3 Ligand: Stem/Progenitor Cell Factors With Overlapping Yet Distinct Activities," *Blood* 91(4): 1101-1134, 1998.

Ray, R. J. et al., "Flt3 ligand supports the differentiation of early B cell progenitors in the presence of IL-11 and IL-7," Manuscript, Feb. 20, 1996.

Chklovskaia, E. et al., "Increased Production of FLT3 Ligand in Leukemia Patients With Chemotherapy-Induced Bone Marrow Suppression," 1996 EHA Abstract Form, Second Meeting of the European Haematology Association, May 29-Jun. 1, 1996.

Wodnar-Filipowicz, A. et al., "Tyrosine kinase receptors and their ligands in aplastic anemia," Manuscript, Feb. 20, 1996.

Hsu, F. et al, "Antigen-Pulsed Dendritic Cells in the Treatment of Patients with B-cell Lymphoma," Abstract # C1-314, Keystone Conference, Taos, NM, Mar. 1995.

Drexhage, H. A., "A Defective Maturation and Function of Dendritic Cells in Type 1 Diabetics," Abstract # C1-204, Keystone Conference, Taos, NM, Mar. 1995.

Fisch, P. et al., "*Ex Vivo* Generation of Functionally Active Antigen Presenting Cells From Peripheral Blood CD34$^+$ Hematopoietic Progenitor Cells in Cancer Patients," Abstract # C1-311, Keystone Conference, Taos, NM, Mar. 1995.

Mayordomo, J. et al., "Bone Marrow-Derived Dendritic Cells Serve as Potent Adjuvants for Peptide-Based Antitumor Vaccines," Abstract # C1-213, Keystone Conference, Taos, NM, Mar. 1995.

Lenz, P. et al., "MHC Class I$^+$/II$^-$ Dendritic Cells Sensitize for Transplantation Immunity," Abstract # C1-318, Keystone Conference, Taos, NM, Mar. 1995.

Ye, Z. et al., "Evaluation of Dendritic Cells in Allogeneic Marrow Grafts," Abstract # C1-130, Keystone Conference, Taos, NM, Mar. 1995.

Thomson, A. W. et al., "Growth of Donor-Derived Dendritic Cells From the Bone Marrow of Murine Liver Allograft Recipients in Response to Granulocyte/Macrophage Colony-Stimulating Factor," Abstract # C1-125, Keystone Conference, Taos, NM, Mar. 1995.

Whalen, R. G. et al., "DNA-Mediated Immunization to the Hepatitis B Surface Antigen: Potential Involvement of Interstitial Dendritic Cells," Abstract # C1-128, Keystone Conference, Taos, NM, Mar. 1995.

Alters, S. et al., Characterization and Gene Modification of Dendritic Cells to be Used for Antigen Presentation, Abstract # C1-302, Keystone Conference, Taos, NM, Mar. 1995.

\* cited by examiner

METHODS OF PREPARING DENDRITIC CELLS WITH FLT3-LIGAND AND ANTIGEN

RELATED APPLICATIONS

This application is a divisional of U.S. patent application Ser. No. 09/154,903, filed Sep. 17, 1998, now abandoned, which is a continuation-in-part of U.S. patent application Ser. No. 08/725,540, filed Oct. 3, 1996, now abandoned, which is continuation-in-part of U.S. patent application Ser. No. 08/539,142, filed Oct. 4, 1995, now abandoned.

FIELD OF THE INVENTION

The present invention relates to a dendritic cell stimulatory factor, to methods of enhancing an immune response in vivo, methods of expanding dendritic cells ex vivo, and to preparations of purified dendritic cells, and to dendritic cell populations useful in the manipulation of T cell-mediated and B-cell mediated immune responses.

BACKGROUND OF THE INVENTION

The objective of vaccination is to provide effective immunity by establishing adequate levels of antibody and a primed population of cells that can rapidly expand on renewed contact with antigen. The first contact with antigen during vaccination must not be injurious to the recipient and thus usually consists of pathogenically-deficient antigen.

A frequent difficulty with active immunization protocols is that the vaccine antigen does not possess sufficient immunogenicity to promote a strong immune response, and therefore a sufficient level of protection against subsequent challenge by the same antigen. In addition, certain antigens may elicit only weak cell-mediated or antibody response. For many antigens, both a strong humoral response and a strong cell-mediated response is desirable.

For decades, researchers have experimented with diverse compounds to increase the immunogenicity of vaccines. Immunopotentiators, also known as adjuvants, of vaccines are compositions of matter that facilitate a strong immune response to a vaccine. In addition, the relatively weak immunogenicity of certain novel recombinant antigens has required adjuvants to be more potent. Vaccine adjuvants have different modes of action, affecting the immune response both quantitatively and qualitatively. Such modes of action can be by mobilizing T cells, acting as depots and altering lymphocyte circulation so that these cells remain localized in draining lymph nodes. They may also serve to focus antigen at the site of immunization, thereby allowing antigen specific T cells and B cells to interact more efficiently with antigen-presenting cells. They may also stimulate proliferation and differentiation of T cells and have effects on B cells, such as enhancing the production of different Ig isotypes. Further, adjuvants may stimulate and affect the behavior of antigen-presenting cells, particularly macrophages, rendering them more effective for presenting antigen to T cells and B cells.

Dendritic cells are a rare and heterogeneous cell population with distinctive morphology and a widespread tissue distribution. A discussion of the dendritic cell system and its role in immunogenicity is provided by Steinman, R. M., *Annu. Rev. Immunol.*, 9:271–296 (1991), incorporated herein by reference. Dendritic cells display an unusual cell surface and can be characterized by the presence of the cell surface markers $CD1a^+$, $CD4^+$, $CD14^-$ $CD86^+$, $CD11c^+$, $DEC-205^+$, $CD14^+$ or $HLA-DR^+$. Dendritic cells have a high capacity for sensitizing MHC-restricted T cells and provide an effective pathway for presenting antigens to T cells in situ, both self-antigens during T cell development and foreign antigens during immunity. Thus, there is growing interest in using dendritic cells ex vivo as tumor or infectious disease vaccine adjuvants. See, for example, Romani, et al., *J. Exp. Med.*, 180:83 (1994). The use of dendritic cells as immunostimulatory agents has been limited due to the low frequency of dendritic cells in peripheral blood, the limited accessibility to lymphoid organs and the dendritic cells' terminal state of differentiation. Dendritic cells originate from CD34+ bone marrow progenitors, and the proliferation and maturation of dendritic cells can be enhanced by the cytokines GM-CSF (sargramostim, Leukine®, Immunex Corporation, Seattle, Wash.), TNF-α, c-kit ligand (also known as stem cell factor (SCF), steel factor (SF), or mast cell growth factor (MGF)) and interleukin-4. Therefore, an agent that stimulated the generation of large numbers of functionally mature dendritic cells in vivo or in vitro would be of wide importance.

SUMMARY OF THE INVENTION

Flt3-ligand ("flt3-ligand") is known to affect hematopoietic stem and progenitor cells. It was surprisingly found that flt3-ligand can also potently stimulate the generation of downstream or intermediate, cells such as myeloid precursor cells, monocytic cells, macrophages, B cells, and dendritic cells from $CD34^+$ bone marrow progenitors and stem cells. The present invention pertains to a method of mobilizing dendritic cells in vivo, expanding dendritic cells ex vivo and to purified preparations of dendritic cells. The preparation of purified dendritic cells according to the invention would potentially find use as vaccine adjuvants. Also included within the embodiments of the invention is a method of preparing antigen-specific T cells using the dendritic cells mobilized with flt3-ligand.

The invention provides for the use of an effective amount of flt3-ligand to increase or mobilize the numbers of intermediate cells in vivo, for example, in the patient's peripheral blood or spleen. While the invention relates to the generation of large numbers of such downstream and intermediate cells (e.g., myeloid cells, monocytic cells and macrophages) from CD34+ cells using flt3-ligand, the focus is particularly on dendritic cells. By increasing the quantity of the patient's dendritic cells, such cells may themselves be used to present antigen to T cells. For example, the antigen may be one that already exists within the patient, such as a tumor antigen, or a bacterial or viral antigen. Flt3-L may be used, therefore, to increase the numbers of dendritic cells in vivo to boost a patient's immune response against existing antigens. The invention further provides for using combination therapy to enhance a patient's immune response. Such combination therapy includes administering flt3-ligand and one or more therapeutic reagents in amounts sufficiently effective to upregulate the patient's immune response. Alternatively, flt3-ligand may be administered prior to, concurrently with or subsequent to administration of an antigen to a patient for immunization purposes. Thus, as a vaccine adjuvant, flt3-ligand can generate large quantities of dendritic cells in vivo to more effectively present the antigen. The overall response is a stronger and improved immune response and more effective immunization to the antigen.

The invention also provides a method of generating large quantities of dendritic cells ex vivo. Following collection of the patient's $CD34^+$ hematopoietic progenitors and stem cells, flt3-ligand can be used to expand such cells in vitro (also known as ex vivo expansion) and to drive such CD34+ cells to differentiate into dendritic cells of the lymphoid or myeloid lineage. The resulting collection of dendritic cells can be administered to a patient to provide a stronger and improved immune response to an antigen. Alternatively, the resulting dendritic cells find use as a vaccine adjuvant and can be administered prior to, concurrently with or subsequent to antigen administration.

The invention also provides a method of generating large quantities of antigen-presenting dendritic cells ex vivo. Following collection of the patient's CD34+ hematopoietic progenitors and stem cells, flt3-ligand can be used to expand such cells in vitro and to drive such CD34+ cells to differentiate into dendritic cells. The resulting collection of dendritic cells is exposed to an antigen and allowed to process and present the antigen in vitro (this procedure is sometimes referred to in the art as "antigen-pulsing"). An alternate method for preparing dendritic cells that present antigen is to transfect the dendritic cells with a gene encoding an antigen-specific polypeptide. Once the dendritic cells express the antigen, the antigen-presenting dendritic cells can be administered to a patient.

The invention also provides for the ex vivo preparation of antigen-specific T cells. Following the procedures described above for preparing large numbers of antigen-presenting dendritic cells ex vivo, the collected antigen-presenting dendritic cells are used to generate antigen-specific T cells from naive T cells that have been collected from a patient. After the antigen has been adequately presented to the T cells generated, the antigen-specific T cells can be administered to the patient.

The invention also provides a method of augmenting an immune response in a patient that has an infectious disease wherein the method comprises the step of administering an amount of flt3-ligand sufficient to increase the patient's number of dendritic cells. Embodiments of methods for augmenting an immune response include administering flt3-ligand in combination therapies with additional active compounds, including but not limited to CD40 binding proteins, 4-1BB-L, antibodies to 4-1BB and combinations thereof The invention also provides a method of augmenting an immune response in a patient that has a cancerous or neoplastic disease wherein the method comprises the step of administering an amount of flt3-ligand sufficient to increase the patient's number of dendritic cells. Embodiments of methods for augmenting an immune response include administering flt3-ligand in combination therapies with additional active compounds, including but not limited to CD40 binding proteins, 4-1BB-L, antibodies to 4-1BB and combinations thereof. Such method provides a means to enhance the patient's tumor-specific immune response.

A method for enhancing a patient's autoimmune tolerance wherein the method comprises the step of administering an amount of flt3-ligand sufficient to increase the patient's number of dendritic cells. Further included are methods for promoting survival of grafts and transplanted tissues and organs.

The methods of the invention can further comprise the use of an effective amount of a cytokine in sequential or concurrent combination with flt3-ligand. Such cytokines include, but are not limited to, interleukins ("ILs") IL-3 and IL-4, a colony stimulating factor ("CSF") selected from the group consisting of granulocyte macrophage colony stimulating factor ("GM-CSF") or GM-CSF/IL-3 fusions, or other cytokines such as TNF-α, CD40 binding proteins (e.g. CD40-L), 4-1BB antagonists (e.g. antibodies immunoreactive with 4-1BB and 4-1BB-1) or c-kit ligand.

The invention further includes a dendritic cell expansion media comprising cell growth media, autologous serum, and flt3-ligand alone or in combination with a cytokine from the group listed above.

DETAILED DESCRIPTION OF THE INVENTION

The invention is directed to the use of flt3-ligand to generate large numbers of intermediate cell types from CD34+ hematopoietic progenitor cells and stem cells. Such intermediate cell types include myeloid cells, monocytic cells, macrophages and dendritic cells. The large numbers of these intermediate cell types are not naturally found in vivo and can be generated by administering flt3-ligand. Such enhancement in overall cell number can augment the immune response to antigen in the host. Another embodiment of the invention is the isolation and use of such intermediate cell types as antigen-presenting cells or the use as vaccine adjuvants. The invention, while particularly focused on the embodiment concerning dendritic cells, is also applicable to myeloid, monocytic and macrophage cell types.

As used herein, the term "flt3-ligand" refers to a genus of polypeptides that are described in U.S. Pat. No. 5,554,512, EP 0627487 A2 and in WO 94/28391, both incorporated herein by reference. A human flt3-ligand cDNA was deposited with the American Type Culture Collection, Rockville, Md., USA (ATCC) on Aug. 6, 1993 and assigned accession number ATCC 69382. The deposit was made under the terms of the Budapest Treaty. Flt3-L can be made according to the methods described in the documents cited above.

The term "IL-3" refers to a genus of interleukin-3 polypeptides as described in U.S. Pat. No. 5,108,910, incorporated herein by reference. Such polypeptides include analogs that have amino acid sequences that are substantially similar to the native human interleukin-3 amino acid sequences disclosed, for example, in EP publ. Nos. 275,598 and 282,185, each incorporated herein by reference. The term "IL-3" also includes analogs and alleles of IL-3 molecules that exhibit at least some of the biological activity in common with native human IL-3. Exemplary analogs of IL-3 are disclosed in EP Publ. No. 282,185. Other forms of IL-3 include human IL-3[Pro$^8$Asp$^{15}$Asp$^{70}$], human IL-3 [Ser$^8$Asp$^{15}$Asp$^{70}$] and human IL-3[Ser$^8$]. A DNA sequence encoding human IL-3 protein suitable for use in the invention is publicly available from the American Type Culture Collection (ATCC) under accession number ATCC 67747. The nomenclature used herein with respect to amino acid sequences in brackets designates which amino acids differ from the native human form. For example, human IL-3 [Ser$^8$Asp$^{15}$Asp$^{70}$] refers to a human IL-3 protein in which amino acid 8 has been changed to a serine residue, amino acid 15 has been changed to an aspartic acid residue and the amino acid 70 has been changed to an aspartic acid residue.

The term "IL-4" refers to a polypeptide as described in Mosley et al., *Cell* 59:335 (1989), Idzerda et al., *J. Exp. Med.* 171:861 (1990) and Galizzi et al., *Intl. Immunol.* 2:669 (1990), each of which is incorporated herein by reference. Such IL-4 polypeptide includes analogs that have an amino acid sequence that is substantially similar to the native human IL-4 amino acid sequences described in Mosley et al., Idzerda et al., and Galizzi et al. and which are biologically active in that they are capable of binding to a IL-4 receptor, transducing a biological signal initiated by binding IL-4 receptor, or cross-reacting with anti-IL-4 antibodies.

The term "IL-4" also includes analogs of native human IL-4 molecules sufficient to retain biological activity of native human IL-4.

As used herein, "GM-CSF" refers to a genus of proteins as described in U.S. Pat. Nos. 5,108,910, and 5,229,496 each of which is incorporated herein by reference. Such proteins include analogs that have an amino acid sequence that is substantially similar to native human GM-CSF amino acid sequences (e.g., as publicly available ATCC 53157 or ATCC 39900), and which are biologically active in that they are capable of binding to a GM-CSF receptor, transducing a biological signal initiated by binding GM-CSF receptor, or cross-reacting with anti-GM-CSF antibodies. Amino acid sequences are disclosed, for example in Anderson, et al., *Proc. Natl. Acad. Sci., USA* 82:6250 (1985). Commercially available GM-CSF (sargramostim, Leukine®) is obtainable from Immunex Corp., Seattle, Wash.). The term "GM-CSF" also includes analogs of the native human GM-CSF molecules described in U.S. Pat. Nos. 5,108,910, and 5,229,496 sufficient to retain biological activity of native human GM-CSF. Exemplary analogs of GM-CSF include, for example, those described in EP Publ. No. 212914 and WO 89/03881, each of which is incorporated herein by reference. Other analogs of GM-CSF also may be used to construct fusion proteins with IL-3. A DNA sequence encoding a particularly preferred GM-CSF protein having potential glycosylation sites removed is publicly available from the ATCC under accession numbers ATCC 67231.

The term "GM-CSF/IL-3 fusion protein" means a C-terminal to N-terminal fusion of GM-CSF and IL-3. The fusion proteins are known and are described in U.S. Pat. Nos. 5,199,942, 5,108,910 and 5,073,627, each of which is incorporated herein by reference. A preferred fusion protein is PIXY321 as described in U.S. Pat. No. 5,199,942.

The term "c-kit ligand" also known as Mast Cell Growth Factor (MGF), Steel Factor or Stem Cell Factor (SCF), refers to a polypeptide described in EP 423,980, which is incorporated herein by reference, and that claims priority from U.S. patent application Ser. No. 07/589,701, filed Oct. 1, 1990. Such c-kit ligand polypeptide includes analogs that have an amino acid sequence that is substantially similar to the native human c-kit ligand amino acid sequences described in EP 423,980 and which are biologically active in that they are capable of binding to a c-kit receptor, transducing a biological signal initiated by binding c-kit receptor, or cross-reacting with anti-c-kit ligand antibodies. The term "c-kit ligand" also includes analogs of native human c-kit ligand molecules sufficient to retain biological activity of native human c-kit ligand.

The term "CD40 binding protein" refers to polypeptides that bind CD40, including but not limited to CD40-L and antibodies immunoreactive with CD40. as described in PCT publications WO 93/08207 and WO 96/40918 each of which is incorporated herein by reference. Such CD40 binding proteins includes analogs that have an amino acid sequence that is substantially similar to the native human CD40-L amino acid sequences described in the PCT publications. and which are biologically active in that they are capable of binding to CD40, transducing a biological signal initiated by binding CD40, or cross-reacting with anti-IL-4 antibodies. The term CD40 binding proteins also includes analogs of native human CD40-L and antibodies reactive with CD40 that are sufficiently homologous to native molecules so as to retain biological activity of native CD40 binding proteins.

The terms "4-1BB-L" and "antibody reactive with 4-1BB" or "antibody to 4-1BB" refer to molecules that are described in U.S. Pat. No. 5,674,704 and Alderson et al. *Eur. J. Immunol.* 24:2219–2227, 1994. which are incorporated herein by reference. 4-1BB-L includes analogs that have an amino acid sequence that is substantially similar to the native 4-1BB-L amino acid sequence described in the above mentioned publication and which are biologically active in that they are capable of binding to 4-1BB or transducing a biological signal initiated by binding 4-1BB, such as inducing a proliferative response in stimulated primary T cells. The terms 4-1BB-L and antibodies to 4-1BB also includes analogs of native 4-1BB-L and analogs of antibodies reactive with 4-1BB that are sufficiently homologous to the native compounds so as to retain biological activity of 4-1BB-L and the described antibodies.

The term "adjuvant" refers to a substance that enhances, augments or potentiates the host's immune response to a vaccine antigen.

The procedure for "ex vivo expansion" of hematopoietic stem and progenitor cells is described in U.S. Pat. No. 5,199,942, incorporated herein by reference. Briefly, the term means a method comprising: (1) collecting $CD34^+$ hematopoietic stem and progenitor cells from a patient from peripheral blood harvest or bone marrow explants; and (2) expanding such cells ex vivo. In addition to the cellular growth factors described in U.S. Pat. No. 5,199,942, other factors such as flt3-ligand, IL-1, IL-3, c-kit ligand, can be used.

The term "immunogenicity" means relative effectiveness of an immunogen or antigen to induce an immune response.

The term "substantially similar" means a variant amino acid sequence preferably that is at least 80% identical to a native amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring variants are also encompassed by the invention. Examples of such variants are proteins that result from alternate mRNA splicing events or from proteolytic cleavage of the native protein, wherein the native biological property is retained.

As used herein, "vaccine" means an organism or material that contains an antigen in an innocuous form. The vaccine is designed to trigger an immunoprotective response. The vaccine may be recombinant or non-recombinant. When inoculated into a non-immune host, the vaccine will provoke active immunity to the organism or material, but will not cause disease. Vaccines may take the form, for example, of a toxoid, which is defined as a toxin that has been detoxified but that still retains its major immunogenic determinants; or a killed organism, such as typhoid, cholera and poliomyelitis; or attenuated organisms, that are the live, but non-virulent, forms of pathogens, or it may be antigen encoded by such organism, or it may be a live tumor cell or an antigen present on a tumor cell.

A variety of cell selection techniques are known for identifying and separating $CD34^+$ hematopoietic stem or progenitor cells from a population of cells. Methods and materials for identifying and selecting such cell types are known. For example, monoclonal antibodies can be used to bind to a marker protein or surface antigen protein found on stem or progenitor cells. Such markers or cell surface antigens for hematopoietic stem cells include CD34 and Thy-1. In one method, antibodies are fixed to a surface, for example, glass beads, and contacted with a mixture of cells suspected of containing stem cells. This permits the antibodies to bind and secure the stem cells to the glass beads. Alternatively, the antibodies can be incubated with the cell mixture and the resulting combination contacted with a surface having an affinity for the antibody-cell complex. Undesired cells and cell matter are removed providing a relatively pure population of stem cells. Stem or progenitor cells having the CD34 marker constitute only about 1% to 3% of the mononuclear cells in the bone marrow. The amount of $CD34^+$ stem or progenitor cells in the peripheral blood is approximately 10- to 100-fold less than in bone marrow.

With regard to the particular aspects of the invention, choosing suitable stem or progenitor cell selection means will depend on the desired phenotype of the cell to be isolated. Hematopoietic stem cells are selectable by virtue of their physical characteristics, such as expressing the membrane-bound flt3 receptor, or having the following cellular markers: CD34 or Thy-1. Monoclonal antibodies that recognize any of these antigens have been described in U.S. Pat. No. 4,714,680 (anti-My-10) incorporated herein by reference, anti-CD34 is commercially available from Becton Dickinson, Franklin Lakes, N.J.), and anti-Thy-1 monoclonal antibodies can be readily generated using the methods described by Dalchau et al., *J. Exp. Med.* 149:576 (1979), incorporated herein by reference. A flt3 receptor binding protein also may be used, such as anti-flt3 monoclonal antibodies or the flt3-ligand. The cell binding protein is brought into contact with the collected cell mixture and the combination is allowed to incubate for a period of time sufficient to permit the binding of the desired cell to the cell binding protein.

An alternative means of selecting the quiescent stem cells is to induce cell death in the dividing, more lineage-committed, cell types using an antimetabolite such as 5-fluorouracil (5-FU) or an alkylating agent such as 4-hydroxycyclophosphamide (4-HC). The non-quiescent cells are stimulated to proliferate and differentiate by the addition of growth factors that have little or no effect on the stem cells, causing the non-stem cells to proliferate and differentiate and making them more vulnerable to the cytotoxic effects of 5-FU or 4-HC. See Berardi et al., *Science,* 267:104 (1995), which is incorporated herein by reference.

Isolation of the hematopoietic stem or progenitor cells can be performed by using, for example, affinity chromatography, antibody-coated magnetic beads, or antibodies fixed to a solid matrix, such as glass beads, flasks, etc. Antibodies that recognize a stem or progenitor cell surface marker can be fused or conjugated to other chemical moieties such as biotin—which can be removed with an avidin or a streptavidin moiety secured to a solid support; fluorochromes useful in fluorescence activated cell sorting (FACS), or the like. Preferably, isolation is accomplished by an immunoaffinity column. Immunoaffinity columns can take any form, but usually comprise a packed bed reactor. The packed bed in these bioreactors is preferably made of a porous material having a substantially uniform coating of a substrate. The porous material, which provides a high surface area-to-volume ratio, allows for the cell mixture to flow over a large contact area while not impeding the flow of cells out of the bed. Typical substrates include avidin and streptavidin, while other conventional substrates can be used. The substrate should, either by its own properties, or by the addition of a chemical moiety, display high-affinity for a moiety found on the cell-binding protein such as a monoclonal antibody. The monoclonal antibodies recognize a cell surface antigen on the cells to be separated, and are typically further modified to present a biotin moiety. It is well-known that biotin has a high affinity for avidin, and the affinity of these substances thereby removably secures the monoclonal antibody to the surface of the packed bed. Such columns are well known in the art, see Berenson, et al., *J. Cell Biochem.,* 10D:239 (1986). The column is washed with a PBS solution to remove unbound material. Target cells can be released from the beads using conventional methods. Immunoaffinity columns of the type described above that utilize biotinylated anti-CD34 monoclonal antibodies secured to an avidin-coated packed bed are described for example, in PCT Publ. No. WO 93/08268. A variation of this method utilizes cell binding proteins, such as the monoclonal antibodies or flt3-ligand as described above, removably-secured to a fixed surface in the isolating means. The bound cell binding protein then is contacted with the collected cell mixture and allowed to incubate for a period of time sufficient to permit isolation of the desired cells.

Alternatively, the monoclonal antibodies that recognize the cell surface antigens can be labeled with a fluorescent label, e.g., chromophore or fluorophore, and separated by cell sorting according to the presence of absence or the amount of labeled product.

The collected $CD34^+$ cells are then exposed to either flt3-ligand alone or flt3-ligand in concurrent or sequential combination with one or more of the following cytokines: GM-CSF, TNF-α, IL-3, IL-4, c-kit-ligand, CD40-L, 4-1BB-L or GM-CSF/IL-3 fusion proteins. $CD34^+$ cells then are allowed to differentiate and commit to cells of the dendritic lineage. The dendritic cells are collected and can either be (a) administered to a patient in order to augment the immune system and T-cell mediated or B-cell mediated immune responses to antigen, (b) exposed to an antigen prior to administration of the dendritic cells into a patient, (c) transfected with a gene encoding an antigen-specific polypeptide or (d) exposed to an antigen and then allowed to process and present the antigen, ex vivo, to T-cells collected from the patient followed by administration of the antigen-specific T-cells to the patient.

More specifically, the invention provides for the use of an effective amount of flt3-ligand to increase or mobilize dendritic cells in vivo, for example, in the patient's peripheral blood or spleen. By increasing the quantity of the patient's dendritic cells, such cells may themselves be used to present antigen to T cells. For example, the antigen may be one that already exists within the patient, such as a tumor antigen, or a bacterial or viral antigen. Flt3-L may be used, therefore, to boost the patient's lymphocyte-mediated (e.g., T cell and B cell mediated) or myeloid-mediated immune response to the already present antigens thus potentially enabling a more effective antigen-presentation to the patient's T cells.

Further, flt3-L may be used in combination therapies with one or more additional agents to enhance an immune response against tumor, viral or bacterial antigens. For example, CD40 binding proteins, which enhance the ability of dendritic cells to process and present antigens to effector T cells, can be administered in combination with flt3-L to dramatically enhance an immune response. Such immune responses can include responses against viral or bacterial antigens that are responsible for infectious diseases and immune responses to tumor antigens. As described in Example 4, a surprising synergy between a CD40 binding protein and flt3-L has been discovered for their combined ability to enhance anti-tumor responses. Representative CD40 binding proteins useful in combination therapy with flt3-L include CD40-L and antibodies immunoreactive with CD40 which are described in PCT publications WO 93/08207 and WO 96/40918.

Additionally, 4-1BB-L and antibodies reactive with 4-1BB, both of which are T-cell co-activation factors, can be administered in combination with flt3-L to dramatically enhance immune responses. 4-1BB-L and antibodies reactive with 4-1BB can be used in combination therapies to enhance immune responses to viral antigens and bacterial antigens responsible for infectious diseases and to enhance immune responses to tumor antigens. More particularly, as described in Example 5, when used in a combination therapy there is a surprising synergy between flt3-L and a 4-1BB-L or antibodies to 4-1BB for anti-tumor immune responses. 4-1BB-L and antibodies reactive with 4-1BB are described in U.S. Pat. No. 5,674,704. The surprising synergy in the above described combination therapies for their ability to dramatically enhance anti-tumor immune responses suggests that stimulating more than one mechanism or more than one cell population is a promising approach to cancer treatment.

In addition to stimulating an immune response to an antigen that already exists within the patient, flt3-ligand may be administered prior to, concurrently with or subsequent to administration of an antigen to a patient for immunization purposes. Thus, as a vaccine adjuvant, flt3-ligand can generate large quantities of dendritic cells in vivo to more effectively present the antigen. The overall response is a stronger and improved immune response and more effective immunization to the antigen. Further, flt3-L may be administered as a vaccine adjuvant in combination with additional active compounds prior to, concurrently with or subsequent to administration of an antigen to a patient for immunization purposes to enhance an immune response against tumor, viral or bacterial antigens. For example, CD40 binding proteins, such as CD40-L and antibodies to CD40 which enhance the ability of dendritic cells to process and present antigens to effector T cells can be administered in combination with flt3-L to dramatically enhance an immune response. Similarly, 4-1BB-L and/or antibodies reactive with 4-1BB can be administered in combination with flt3-L to enhance an immune response and provide more effective immunization to the antigen.

The systemic administration of flt3-ligand not only is effective as a vaccine adjuvant, but as discussed supra., is effective in augmenting an immune response against previously existing antigens. For example, the inventors have shown that flt3-ligand administration to tumor-bearing mice results in at least a significant decrease in the growth rate of the tumor, and can result in tumor regression in a large proportion of the mice. The data are presented in more detail in Example 3. Flt3-L therefore is an important cytokine in the generation of an effective immune response in vivo against antigen. Data in Example 4 and Example 5 demonstrate that when used in combination therapy with additional agents, flt3-L can provide a dramatically enhanced immune response in vivo against antigen.

Because of its ability to generate dendritic cells, flt3-ligand also finds use in promoting the survival of transplanted tissue or organs. When allogeneic organs or other tissue is transplanted into a host they can transfer stem cells, immature dendritic cells, and mature dendritic cells from the donor. These cells are called passenger cells and such cells can graft into the hematopoietic system of the host. Additionally, stem cells, immature dendritic cells, and mature dendritic cells from the host may graft to the donor organ or tissue. It is possible then to establish a tolerance between the graft and the host since the immature dendritic cells from the host and donor tissue interact with T-cells from the "other side." Such interaction may include the deletion of T-cells that recognize the major histocompatability complex (MHC) that the dendritic cells express. In this way, the donor cells are "screened" so that they fail to recognize and react against the host (i.e., no graft versus host disease) and the host T-cells are screened so that they fail to recognize and react against the graft (i.e., no graft rejection). Thus, a mutual tolerance can be achieved, and the graft is accepted. Administration of flt3-ligand to the host or donor prior to transplantation would generate increased numbers of dendritic cells in such host or donor and permit increased tolerance and survival of the graft.

For the growth and culture of dendritic cells, a variety of growth and culture media can be used, and the composition of such media can be readily determined by a person having ordinary skill in the art. Suitable growth media are solutions containing nutrients or metabolic additives, and include those that are serum-depleted or serum-based. Representative examples of growth media are RPMI, TC 199, Iscoves modified Dulbecco's medium (Iscove, et al., *F.J. Exp. Med.*, 147:923 (1978)), DMEM, Fischer's, alpha medium, NCTC, F-10, Leibovitz's L-15, MEM and McCoy's. Particular examples of nutrients that will be readily apparent to the skilled artisan include, serum albumin, transferrin, lipids, cholesterol, a reducing agent such as 2-mercaptoethanol or monothioglycerol, pyruvate, butyrate, and a glucocorticoid such as hydrocortisone 2-hemisuccinate. More particularly, the standard media includes an energy source, vitamins or other cell-supporting organic compounds, a buffer such as HEPES, Tris, that act to stabilize the pH of the media, various inorganic salts. Particular reference is made to PCT Publ. No. WO 95/00632, wherein a variety of serum-free cellular growth media is described, such disclosure is incorporated herein by reference.

For any of the ex vivo methods of the invention, peripheral blood progenitor cells (PBPC) and peripheral blood stem cells (PBSC) are collected using apheresis procedures known in the art. See, for example, Bishop et al., *Blood*, vol. 83, No. 2, pp. 610–616 (1994). Briefly, PBPC and PBSC are collected using conventional devices, for example, a Haemonetics® Model V50 apheresis device (Haemonetics, Braintree, Mass.). Four-hour collections are performed typically no more than five times weekly until, for example, approximately $6.5 \times 10^8$ mononuclear cells (MNC)/kg patient are collected. The cells are suspended in standard media and then centrifuged to remove red blood cells and neutrophils.

Cells located at the interface between the two phases (also known in the art as the buffy coat) are withdrawn and resuspended in HBSS. The suspended cells are predominantly mononuclear and a substantial portion of the cell mixture are early stem cells. The resulting stem cell suspension then can be contacted with biotinylated anti-CD34 monoclonal antibodies or other cell-binding means. The contacting period is maintained for a sufficient time to allow substantial interaction between the anti-CD34 monoclonal antibodies and the CD34 antigens on the stem cell surface. Typically, times of at least one hour are sufficient. The cell suspension then is brought into contact with the isolating means provided in the kit. The isolating means can comprise a column packed with avidin-coated beads. Such columns are well known in the art, see Berenson, et al., *J. Cell Biochem.*, 10D:239 (1986). The column is washed with a PBS solution to remove unbound material. Target stem cells can be released from the beads and from anti-CD34 monoclonal antibody using conventional methods. The stem cells obtained in this manner can be frozen in a controlled rate freezer (e.g., Cryo-Med®, Mt. Clemens, Miss.), then stored in the vapor phase of liquid nitrogen. Ten percent dimethylsulfoxide can be used as a cryoprotectant. After all collections from the donor have been made, the stem cells are thawed and pooled. Aliquots containing stem cells, growth medium, such as McCoy's 5A medium, 0.3% agar, and at least one of the expansion factors: recombinant human GM-CSF, IL-3, recombinant human flt3-ligand, and recombinant human GM-CSF/IL-3 fusion molecules (PIXY321) at concentrations of approximately 200 U/mL, are cultured and expanded at 37° C. in 5% $CO_2$ in fully humidified air for 14 days. Optionally, human IL-1α or IL-4 may be added to the cultures. The most preferred combination of expansion factors comprises flt3-ligand plus either IL-3 or a GM-CSF/IL-3 fusion protein.

For in vivo administration to humans, flt3-ligand can be formulated according to known methods used to prepare pharmaceutically useful compositions. Flt3-L can be combined in admixture, either as the sole active material or with other known active materials (e.g. CD40 binding proteins, such as CD40-L or antibodies reactive with CD40, and 4-1BB-L or antibodies reactive with 4-1BB), with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain flt3-ligand complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of flt3-ligand.

Flt3-L can be administered topically, parenterally, or by inhalation. The term "parenteral" includes subcutaneous injections, intravenous, intramuscular, intracisternal injection, or infusion techniques. These compositions will typically contain an effective amount of the flt3-ligand, alone or in combination with an effective amount of any other active material, e.g. those described above. Effective amounts, or dosages, and desired concentrations of flt3-L and active compounds, e.g. CD40-L and/or 4-1BB-L, or antibodies reactive with 4-1BB, contained in the compositions may vary depending upon many factors, including the intended use, patient's body weight and age, and route of administration. Preliminary doses can be determined according to animal tests, and the scaling of dosages for human administration can be performed according to art-accepted practices. Keeping the above description in mind, typical dosages of flt3-ligand may range from about 10 µg per square meter to about 1000 µg per square meter. A preferred dose range is on the order of about 100 µg per square meter to about 300 µg per square meter.

In addition to the above, the following examples are provided to illustrate particular embodiments and not to limit the scope of the invention.

EXAMPLE 1

Generation of Dendritic Cells

This Example describes a method for using flt3-ligand to generate large numbers of dendritic cells ex vivo. Cells having the $CD34^+$ phenotype are isolated as described above, for example, first by generating a buffy coat of cells using a procedure described supra. Cells from the buffy coat are then incubated with a CD34 specific monoclonal antibody. The $CD34^+$ cells which are selected then are cultured in McCoy's enhanced media with 20 ng/ml each of GM-CSF, IL-4, TNF-α, or 100 ng/ml flt3-ligand or c-kit ligand. The culture is continued for approximately two weeks at 37° C. in 10% $CO_2$ in humid air. Cells then are sorted by flow cytometry for $CD1a^+$ and $HLA-DR^+$ expression. The combination of GM-CSF, IL-4 and TNF-α, resulted in a six to seven-fold increase in the number of cells obtained after two weeks of culture. The combination of flt3-ligand and c-kit ligand resulted in an additive 12-13-fold increase in absolute cell numbers. This correlated with an 18-fold expansion with either flt3-ligand or c-kit ligand or to a 34-fold expansion with the combination of flt3-ligand and c-kit ligand. Phenotypic analysis of the cells showed that between 60–70% of the cells were $HLA-DR^+$, $CD86^+$, with 40–50% of the cells expressing CD1a in all factor combinations examined. The addition of flt3-ligand increased the absolute number of $CD1a^+$ cells by 5-fold. c-Kit ligand increased those cells by 6.7-fold and the combination of flt3-ligand and c-kit ligand by 11-fold. Functional analysis of the resultant cells in an MLR revealed that the presence of flt3-ligand or c-kit ligand did not affect the stimulatory capacity of the resultant dendritic cells while increasing the numbers attained.

EXAMPLE 2

Use of Flt3-L in Dendritic Cell Expansion

This Example describes a method for using flt3-ligand for dendritic cell expansion. Prior to cell collection, it may be desirable to mobilize or increase the numbers of circulating PBPC and PBSC. Mobilization can improve PBPC and PBSC collection, and is achievable through the intravenous administration of flt3-ligand or sargramostim (Leukine®, Immunex Corporation, Seattle, Wash.) to the patients prior to collection of such cells. Other growth factors or reactive agents such as CSF-1, GM-CSF, c-kit ligand, G-CSF, EPO, IL-1, IL-2, IL-3, IL-4, IL-5, IL-6, IL-7, IL-8, IL-9, IL-10, IL-11, IL-12, IL-13, IL-14, IL-15, GM-CSF/IL-3 fusion proteins, LIF, FGF, CD40 binding proteins, 4-1BBL and combinations thereof, can be likewise administered in sequence, or in concurrent combination with flt3-ligand. Mobilized or non-mobilized PBPC and PBSC are collected using apheresis procedures known in the art. See, for example, Bishop et al., *Blood*, vol. 83, No. 2, pp. 610–616 (1994). Briefly, PBPC and PBSC are collected using conventional devices, for example, a Haemonetics® Model V50 apheresis device (Haemonetics, Braintree, Mass.). Four-hour collections are performed typically no more than five times weekly until approximately $6.5 \times 10^8$ mononuclear cells (MNC)/kg patient are collected. Aliquots of collected PBPC and PBSC are assayed for granulocyte-macrophage colony-forming unit (CFU-GM) content by diluting approximately 1:6 with Hank's balanced salt solution without calcium or magnesium (HBSS) and layering over lymphocyte separation medium (Organon Teknika, Durham, N.C.). Following centrifugation, MNC at the interface are collected, washed and resuspended in HBSS. One milliliter aliquots containing approximately 300,000 MNC, modified McCoy's 5A medium, 0.3% agar, 200 U/mL recombinant human GM-CSF, 200 u/mL recombinant human IL-3, and 200 u/mL recombinant human G-CSF are cultured at 37° C. in 5% $CO_2$ in fully humidified air for 14 days. Optionally, flt3-ligand or GM-CSF/IL-3 fusion molecules (PIXY 321) may be added to the cultures. These cultures are stained with Wright's stain, and CFU-GM colonies are scored using a dissecting microscope (Ward et al., *Exp. Hematol.*, 16:358 (1988). Alternatively, CFU-GM colonies can be assayed using the CD34/CD33 flow cytometry method of Siena et al., *Blood*, Vol. 77, No. 2, pp 400–409 (1991), or any other method known in the art.

CFU-GM containing cultures are frozen in a controlled rate freezer (e.g., Cryo-Med®, Mt. Clemens, Miss.), then stored in the vapor phase of liquid nitrogen. Ten percent dimethylsulfoxide can be used as a cryoprotectant. After all collections from the patient have been made, CFU-GM containing cultures are thawed and pooled. The thawed cell collection is contacted with flt3-ligand either alone, sequentially or in concurrent combination with other cytokines listed above. Such exposure to flt3-ligand will drive the CFU-GM to dendritic cell lineage. The dendritic cells are reinfused intravenously to the patient.

EXAMPLE 3

Use of Flt3-L in Augmenting Anti-Tumor Immune Responses

This Example describes a method for using flt3-L to augment anti-tumor immune responses in vivo. Female C57BL/10J (B10) mice (The Jackson Laboratory, Bar Harbor, Me.) were injected with $5 \times 10^5$ viable B10.2 or B10.5 fibrosarcoma tumor cells by intradermal injection in a midline ventral position in a total volume of 50 µl. The fibrosarcoma B10.2 and B10.5 lines are of B10 origin and have been described previously, see Lynch et a, *Euro. J. Immunol.*, 21:1403 (1991) incorporated herein by reference. The fibrosarcoma B10.2 line was induced by subcutaneous implantation of a paraffin pellet containing 5 mg of methylcholanthrene, and the B10.5 cell line was induced by chronic exposure to ultraviolet radiation. The tumor cell lines were maintained in vitro in α-modified MEM containing 5% FBS, 2 nM L-glutamine, 50 U/ml penicillin and 50 µg/ml streptomycin. Recombinant human flt3-L (10 µg/injection) was administered on a daily basis over a 19-day period (unless otherwise noted) by subcutaneous injection in a total volume of 100 µl. Control mice were similarly injected with a similar volume of buffer containing 100 ng MSA. Tumor growth rates were determined by plotting the tumor size versus time after tumor challenge. Tumor size was calculated as the product of two perpendicular diameters, measured by calipers, and is expressed as the mean tumor size of only those mice bearing a tumor within a particular treatment group. The number of mice bearing tumors compared to the number challenged for each treatment group at the termination of an experiment are shown in the data below.

From Table I, the data is a compilation of six different experiments wherein tumor-bearing mice were either treated with flt3-ligand or MSA. Complete tumor regression was observed in 19 of 50 flt3-ligand treated mice compared to 1 of 30 in MSA-treated mice (p<0.0001 using Fishers Exact Test). The observation that the rate of tumor growth in flt3-ligand treated mice (mean tumor size in tumor-bearing mice at week 5 post-tumor challenge was 60+/–8 $mm^2$) was significantly reduced compared to MSA-treated mice (mean tumor size at week 5 post-tumor challenge was 185+/–17 $mm^2$) was also confirmed (p.0001 by Analysis of Variance).

TABLE I

Fibrosarcoma +/– Flt3-L Composite of Six Experiments Tumor Size ($mm^2$)

| Weeks Post Tumor Challenge | MSA Control (100 ng/day) | Standard Error | Flt3-L (10 µg/day) | Standard Error |
| --- | --- | --- | --- | --- |
| 0 | 0 | 0 | 0 | 0 |
| 1 | 25 | 2.6 | 24 | 2.2 |
| 2 | 62 | 7.5 | 49 | 3.6 |
| 3 | 98 | 10.6 | 49 | 3.9 |
| 4 | 149 | 14.5 | 50 | 5 |
| 5 | 185 | 16.8 | 60 | 8.4 |

Tumor size was sharply retarded with flt3-L compared to the control. Therefore, the data show that flt3-L is an important cytokine in the augmentation of the immune response against foreign antigens, and in particular against cancer.

EXAMPLE 4

Use of Flt3-L in Combination Therapy to Activate an Immune Response

This Example demonstrates the use of flt3-L in combination with a CD40 binding protein to augment anti-tumor immune responses in vivo. In one study C57BL/10J (B10) mice (The Jackson Laboratory, Bar Harbor, Me.) were injected intradermally with $5 \times 10^5$ cells of the viable B10.2 fibrosarcoma tumor cell line described in Example 3 above. In one set of mice, beginning on the same day as the tumor injections, recombinant human flt3-L (10 µg/injection/day) was administered to each mouse on a daily basis over a 20-day period by subcutaneous injection in a total volume of 100 µl. In another set of mice each mouse was injected with the same volume and amount of CD40-L each day for 20 days. In a third set, each mouse was injected with a combination of 10 µg flt3-L and 10 µg of CD40-L per day for 20 days. Control mice were similarly injected with a similar volume of buffer containing 100 ng MSA. Tumor growth rates were determined measuring tumor size each week after tumor challenge over a 5 week period. Tumor size was calculated as the product of two perpendicular diameters, measured by calipers, and is expressed as the mean tumor size. Only mice bearing tumors within each group were considered in determining the mean size. The frequency of tumor rejections was also determine and expressed as the number of mice bearing no tumors compared to the number challenged for each treatment group at the termination of an experiment.

Table II provides data in the form of mean tumor size in tumor bearing animals, calculated once a week over a 5 week period post challenge. Table III details the percent frequency of tumor rejection for each set of mice over a 6 week period post challenge. The data demonstrate that for tumor bearing mice, the mean tumor size mice in mice treated with flt3-L and flt3-L in combination with CD40-L is comparable and less than the tumor size in tumor bearing control mice. Significantly, however, mice receiving the combination therapy experienced significantly higher frequency of tumor rejection than mice receiving flt3-L or CD40-L alone. More specifically, 5 weeks post challenge, 62.5% of the mice receiving the combination therapy experienced complete tumor rejection. By contrast, at 5 weeks post challenge, 25% of the mice receiving flt3-L alone experienced complete tumor rejection and none of the mice receiving CD40-L alone experience complete tumor rejection.

TABLE II

B10.2 Fibrosarcoma
Tumor Size (mm$^2$)

| Weeks Post Tumor Challenge | MSA Control (100 ng/day) | Flt3-L (10 μg/day) | CD40-L (10 μg/day) | Flt3-L/CD40-L (each 10 μg/day) |
|---|---|---|---|---|
| 1 | 28 | 24 | 25 | 23 |
| 2 | 68 | 51 | 62 | 46 |
| 3 | 135 | 64 | 107 | 59 |
| 4 | 239 | 81 | 212 | 80 |
| 5 | 351 | 117 | 343 | 137 |
| 6 | | | | |

TABLE III

B10.2 Fibrosarcoma
% Frequency of Tumor Rejection

| Weeks Post Tumor Challenge | MSA Control (100 ng/day) | Flt3-L (10 μg/day) | CD40-L (10 μg/day) | Flt3-L/CD40-L (each 10 μg/day) |
|---|---|---|---|---|
| 1 | 0 | 0 | 0 | 0 |
| 2 | 0 | 0 | 0 | 0 |
| 3 | 0 | 0 | 0 | 0 |
| 4 | 0 | 12.5 | 0 | 50 |
| 5 | 0 | 25 | 0 | 62.5 |
| 6 | 0 | 25 | 0 | 62.5 |

In another study C3H/HeN mice were injected intradermally with 5×10$^5$ cells of a very aggressive tumor, the 87 fibrosarcoma tumor cell line. In one set of mice, beginning the day after the tumor injections, recombinant human flt3-L (10 μg/injection/day) was administered to each mouse on a daily basis over a 20-day period by subcutaneous injection. In another set of mice, each mouse was injected with the same volume and amount of CD40-L each day, beginning at day 7 and continuing to day 20. In a third set, each mouse received a combination therapy of CD40-L and flt3-L. The combination therapy included 10 μg/day of flt3-L beginning the day after tumor injection and continuing until day 20 and 10 μg/day of CD40-L beginning at day 7 and continuing until day 20. Mice in a control group were similarly injected with a similar volume of buffer containing 100 ng MSA. Tumor growth rates were determined by measuring tumor size each week post tumor challenge over a 6 week period. Tumor size was calculated as the product of two perpendicular diameters, measured by calipers, and is expressed as the mean tumor size. Only mice bearing tumors were considered in determining the mean size. The frequency of tumor rejections was also determine and expressed as the number of mice bearing no tumors compared to the number challenged for each treatment group at the termination of an experiment.

Table IV provides data in the form of mean tumor size in tumor bearing animals, calculated once a week over a 6 week period post challenge. Table V details the percent frequency of tumor rejection for each set of mice over a 6 week period post challenge. The data demonstrate that for tumor bearing mice, the mean tumor size mice in mice treated with flt3-L in combination with CD40-L is significantly less than the tumor size in tumor bearing control mice and mice bearing tumors in the groups receiving only flt3-L and only CD40-L. Significantly, mice receiving the combination therapy experienced significantly higher frequency of tumor rejection than mice receiving flt3-L or CD40-L alone. More specifically, 6 weeks post challenge, 50% of the mice receiving the combination therapy experienced complete tumor rejection. By contrast, at 6 weeks post challenge, 10% of the mice receiving flt3-L alone experienced complete tumor rejection and none of the mice receiving CD40-L alone experience complete tumor rejection.

The observations described above demonstrate that a flt3-L and CD40-L combination therapy can dramatically up-regulate anti-tumor immune responses in vivo. The data indicate that a synergy exists between flt3-L and the CD40 binding protein, CD40-L, in that when used alone flt3-L and CD40-L show little or no tumor rejection. In combination the rejection is dramatic. Studies also demonstrated that using a combination of flt3-L and CD40-L resulted in IL-12 expression on tumor cells. This contrasts with the results of studies using flt3-L alone and CD40-L alone which did not indicate promotion of IL-12 expression.

TABLE IV

87 Fibrosarcoma
Tumor Size (mm$^2$)

| Weeks Post Tumor Challenge | MSA Control (100 ng/day) | Flt3-L (10 μg/day) | CD40-L (10 μg/day) | Flt3-L/CD40-L (each 10 μg/day) |
|---|---|---|---|---|
| 1 | 23 | 23 | 30 | 29 |
| 2 | 54 | 53 | 49 | 34 |
| 3 | 108 | 94 | 87 | 44 |
| 4 | 176 | 159 | 144 | 67 |
| 5 | 286 | 256 | 247 | 115 |
| 6 | 465 | 439 | 410 | 239 |

TABLE V

87 Fibrosarcoma
% Frequency of Tumor Rejection

| Weeks Post Tumor Challenge | MSA Control (100 ng/day) | Flt3-L (10 μg/day) | CD40-L (10 μg/day) | Flt3-L/CD40-L (each 10 μg/day) |
|---|---|---|---|---|
| 1 | 0 | 0 | 0 | 0 |
| 2 | 0 | 0 | 0 | 0 |
| 3 | 0 | 0 | 0 | 30 |

TABLE V-continued

87 Fibrosarcoma
% Frequency of Tumor Rejection

| Weeks Post Tumor Challenge | MSA Control (100 ng/day) | Flt3-L (10 μg/day) | CD40-L (10 μg/day) | Flt3-L/CD40-L (each 10 μg/day) |
|---|---|---|---|---|
| 4 | 0 | 10 | 0 | 40 |
| 5 | 0 | 10 | 0 | 50 |
| 6 | 0 | 10 | 0 | 50 |

EXAMPLE 5

Use of Flt3-L in Combination Therapy with to Activate an Immune Response

This Example demonstrates the use of flt3-L in combination with an antibody reactive with 4-1BB to augment anti-tumor immune responses in vivo. In one study C57BL/10J (B10) mice (The Jackson Laboratory, Bar Harbor, Me.) were injected intradermally with $5 \times 10^5$ cells of the viable B10.2 fibrosarcoma tumor cell line described in Example 3 above. In one set of mice, beginning on the same day as the tumor injections, recombinant human flt3-L (10 μg/injection/day) was administered to each mouse on a daily basis over a 14-day period by subcutaneous injection in a total volume of 100 μl. In another set of mice each mouse was injected IP with 100 μg of rat anti mu 4-1BB clone on days 3 and 6 post tumor challenge. In a third set, each mouse was injected with 100 μg rat anti mu 4-1BB clone on days 13 and 16. A fourth set of mice were injected with a combination of 10 μg flt3-L on days 1–14 and 100 μg of rat anti mu 4-1BB clone on days 13 and 16 post tumor challenge. Control mice were injected with buffer containing 100 ng MSA. Tumor growth rates were determined measuring tumor size each week after tumor challenge over a 5 week period. Tumor size was calculated as the product of two perpendicular diameters, measured by calipers, and is expressed as the mean tumor size in $mm^2$. Only mice bearing tumors within each group were considered in determining the mean tumor size. The percent incidence of tumors was also determine and expressed as the number of mice bearing tumors compared to the number challenged for each treatment group at the termination of an experiment.

Table VI provides data in the form of mean tumor size in tumor bearing animals, calculated once a week over an 8 week period post challenge. Table VII details the percent incidence of tumors for each set of mice over an 8 week period post challenge. The data demonstrate that for tumor bearing mice, the mean tumor size in mice treated with flt3-L alone and the mean tumor size in mice treated with the anti 4-1BB regimen are similar. However, when flt3-L in combination with an antibody reactive with 4-1BB is administered to mice, mean tumor size in tumor bearing mice is remarkably decreased. Specifically, at 5 weeks post tumor challenge, mice receiving the combination therapy had a mean tumor size of 0, indicating 100% tumor rejection. This data is supported by the numbers in Table VII which demonstrate that mice receiving the combination therapy experienced significantly lower incidence of tumors than mice receiving flt3-L or 4-1BB antibody alone. More specifically, at 5 weeks post challenge, all of the mice receiving the combination therapy experienced complete tumor rejection (0% tumor incidence). By contrast, at 5 weeks post challenge, 70% of the mice receiving flt3-L alone had tumors and 50% and 70% of the mice receiving 4-1BB antibody alone had tumors. This data provides evidence that anti-4-1BB synergizes with flt3-L in providing immune response.

TABLE VI

B10.2 Fibrosarcoma
Tumor Size ($mm^2$)

| Weeks Post Tumor Challenge | MSA Control (100 ng/day) | Flt3-L (10 μg/day) | anti 4-1BB (100 μg, day 3 and 6) | anti 4-1BB (100 μg days 13 and 16) | anti 4-1BB(days 13 and 16) and flt3-L |
|---|---|---|---|---|---|
| 1 | 28 | 15 | 25 | 25 | 20 |
| 2 | 60 | 35 | 55 | 60 | 35 |
| 3 | 85 | 35 | 55 | 40 | 15 |
| 4 | 125 | 45 | 60 | 50 | 8 |
| 5 | 200 | 55 | 70 | 40 | 0 |
| 6 | 280 | 95 | 80 | 45 | 0 |
| 7 |  | 125 | 130 | 115 | 0 |
| 8 |  |  | 160 | 135 | 0 |

TABLE VII

B10.2 Fibrosarcoma
% Tumor Incidence

| Weeks Post Tumor Challenge | MSA Control (100 ng/day) | Flt3-L (10 μg/day) | anti 4-1BB (days 3 and 6) | anti 4-1BB (days 13 and 16) | Flt3-L and anti 4-1BB (days 13 and 16) |
|---|---|---|---|---|---|
| 1 | 100 | 100 | 100 | 100 | 100 |
| 2 | 100 | 100 | 100 | 100 | 90 |
| 3 | 100 | 100 | 90 | 100 | 80 |
| 4 | 100 | 90 | 80 | 50 | 30 |
| 5 | 100 | 70 | 70 | 50 | 0 |

TABLE VII-continued

| | B10.2 Fibrosarcoma % Tumor Incidence | | | | |
|---|---|---|---|---|---|
| Weeks Post Tumor Challenge | MSA Control (100 ng/day) | Flt3-L (10 µg/day) | anti 4-1BB (days 3 and 6) | anti 4-1BB (days 13 and 16) | Flt3-L and anti 4-1BB (days 13 and 16) |
| 6 | 100 | 60 | 60 | 40 | |
| 7 | 100 | 60 | 50 | 20 | |
| 8 | 100 | 60 | 50 | 20 | |

The invention claimed is:

1. An in vitro method of preparing a dendritic cell population comprising the steps of:
    (a) contacting hematopoietic stem cells, progenitor cells, or hematopoietic stem and progenitor cells with a growth factor or cytokine in vitro, wherein the growth factor or cytokine consists of flt3-ligand in an amount sufficient to generate a dendritic cell population;
    (b) exposing the dendritic cells to an antigen; and
    (c) allowing the dendritic cells to process and express the antigen.

2. An in vitro method of preparing a dendritic cell population comprising the steps of:
    (a) contacting hematopoietic stem cells, progenitor cells, or hematopoietic stem and progenitor cells with a growth factor or cytokine in vitro, wherein the growth factor or cytokine consists of flt3-ligand and GM-CSF in amounts sufficient to generate a dendritic cell population;
    (b) exposing the dendritic cells to an antigen; and
    (c) allowing the dendritic cells to process and express the antigen.

3. The method according to claim 1 wherein the flt3-ligand is human flt3-ligand.

4. The method according to claim 2 wherein the flt3-ligand is human flt3-ligand.

5. The method according to claim 2 wherein the GM-CSF is human GM-CSF.

* * * * *